United States Patent [19]

Dunn et al.

[11] Patent Number: 4,731,084
[45] Date of Patent: Mar. 15, 1988

[54] PROSTHETIC LIGAMENT

[75] Inventors: Richard L. Dunn, Birmingham; Danny H. Lewis, Hartselle, both of Ala.; Thomas W. Sander; Richard W. Treharne, III, both of Memphis, Tenn.

[73] Assignee: Richards Medical Company, Memphis, Tenn.

[21] Appl. No.: 840,298

[22] Filed: Mar. 14, 1986

[51] Int. Cl.$^4$ .............................................. A61F 2/08
[52] U.S. Cl. ...................................... 623/13; 623/16
[58] Field of Search ................... 623/13, 16, 1, 2, 66; 128/335.5, 334

[56] References Cited

U.S. PATENT DOCUMENTS

| | | | |
|---|---|---|---|
| 4,149,277 | 4/1979 | Bokros | 623/13 |
| 4,301,551 | 11/1981 | Dore et al. | 623/13 |
| 4,550,730 | 11/1985 | Shalaby et al. | 128/335.5 |
| 4,584,722 | 4/1986 | Levy et al. | 623/13 |
| 4,587,163 | 5/1986 | Zachariades | 623/13 X |
| 4,610,688 | 9/1986 | Silvestrini et al. | 623/2 X |
| 4,662,886 | 5/1987 | Moorse et al. | 623/13 |

OTHER PUBLICATIONS

C. Frank et al., "Normal Ligament Properties and Ligament Healing", 196 Clinical Orthopaedics and Related Research, Synthetic Ligaments and Tendons, (H. Alexander & A. Weiss eds. Jun. 1985) at 15.

D. Butler et al., "On the Interpretation of Our Anterior Cruciate Ligament Data", Clinical Orthopaedics, supra at 26.

G. Strum & Larson, "Clinical Experience and Early Results of Carbon Fiber Augmentation of Anterior Cruciate Reconstruction of the Knee," Clinical Orthopaedics, supra at 26.

G. K. McPherson et al., "Experimental Mechanical and Histologic Evaluation of the Kennedy Ligament Augmentation Device", Clinical Orthopaedics, supra at 186.

C. Bolton & W. Bruchman, "The Gore-Tex ™ Expanded Polytetrafluoroethylene Prosthetic Ligament, An In Vitro and In Vivo Evaluation", Clinical Orthopaedics, supra at 202.

"New Technology, New Horizons", Allied Corporation, 1985 Product Brochure for Spectra-900 ®.

Prosthetic Ligament Reconstruction of the Knee, 2d Annual Symposium Department of Continuing Education in Health Sciences, UCLA Extension, and the School of Medicine, UCLA (Mar. 21-24, 1985).

C. Peterson et al., "A Segmented Polyurethane Composite Prosthetic Anterior Cruciate Ligament In Vivo Study", 19 Journal of Biomedical Materials Research 589 (1985).

Primary Examiner—Richard J. Apley
Assistant Examiner—Alan W. Cannon
Attorney, Agent, or Firm—Kirkpatrick & Lockhart

[57] ABSTRACT

A nonaugmented prosthetic ligament for permanently replacing a natural ligament spanning first and second body members, such as the femur and tibia includes a load bearing member formed from a plurality of biocompatible polyolefin fibers positioned at angles of from 0° to 55° relative to the longitudinal axis of the load bearing member. Each fiber is less than 100 microns in diameter and has a tensile strength greater than or equal to about 50,000 psi. The load bearing member may be used alone or may be formed into a hollow braid having a core disposed within the hollow portion of the braid to provide shape for the load bearing member. A sheath may be friction fit or molded onto the exterior of the load bearing member to prevent abrasion of the fibers.

17 Claims, 5 Drawing Figures

PROSTHETIC LIGAMENT

BACKGROUND OF THE INVENTION

1. Field of the Invention

The present invention relates generally to prosthetic devices and more particularly to a permanent prosthetic ligament.

2. Description of the Prior Art

Attempts to repair or replace damaged ligaments have been varied and generally inadequate for immediately restoring full strength and stability to the involved joint. Workers in the field have transferred natural tissue from other parts of a patient's body to the involved joint. Synthetic materials have also been used to augment natural tissue transfers. A number of techniques employing carbon fiber-type or polypropylene augmentation devices are described in 196 CLINICAL ORTHOPAEDICS AND RELATED RESEARCH, SYNTHETIC LIGAMENTS AND TENDONS, (H. Alexander & A. Weiss eds. June 1985). For example, a flat strap-like braid of polypropylene fibers was used to augment natural tissue grafts in studies conducted on goats. See G. McPherson et al. "Experimental Mechanical and Histologic Evaluation of the Kennedy Ligament Auogmentation Device", CLINICAL ORTHOPAEDICS supra at 186. The time required for the recipient to return to normal activity is generally about one year or longer.

As an alternative to natural tissue grafts, xenografts, tissue grafts from a species other than the recipient species, have been implanted to replace natural ligaments. Like the natural tissue grafts and the augmentation devices, xenografts have tended to be unpredictable in the long term for restoring full strength and stability to the involved joint.

Another type of prosthetic ligament relies on bone ingrowth to aid in the attachment of the ligament to bone. Bone growth strengthens the attachment but requires about six months to complete. In the meantime, the recipient's mobility should be restricted. Dahlen et al. U.S. Pat. No. 4,187,558, which issued on Feb. 12, 1980, describes a flexible braid made of polyethylene terephthalate, encased in silicone rubber. A velour covered collar at one or both ends of the braid aids in attachment to the bone and promotes bone ingrowth to anchor the device.

Several permanent, nonaugmented prosthetic ligaments have been developed. Dore U.S. Pat. No. 4,301,551, which issued on Nov. 24, 1981 describes a deformable silicone core surrounded by a tensionable wrapping of stainless steel threads wound in a helical angle about the core. The core is the load bearing member and is capable of large elastic deformation in response to compression by the threads when the device is stretched. Two rigid plastic rods, one at each end of the core, connect the device to the bones of a joint.

Treace U.S. Pat. No. 3,953,896, which issued on May 4, 1976 describes a prosthetic ligament made of a flexible high molecular weight polyethylene rod. Stainless steel sleeves and polyethylene nuts on each end of the flexible rod hold the prosthetic ligament to the bones.

A third permanent, nonaugmented prosthetic ligament reported by C. Bolton and W. Bruchman, "The GORE-TEX TM Expanded Polytetrafluoroethylene Prosthetic Ligament", CLINICAL ORTHOPAEDICS supra at 202, is constructed of bundles of Gore-Tex ® fibers arranged in a braided configuration. The braid is fixed by bone screws placed through eyelets at each end of the braid.

The goal of ligament replacement is to permit the recipient to return to his or her full range of activity as soon as possible. To that end, researchers have attempted by several means to mimic some of the parameters of strength, flexibility, extension and/or recovery found in natural ligaments. Natural ligaments are bands of flexible fibrous connective tissue which join bones or hold organs in place. The mechanical properties of a natural ligament were reported by D. Butler et al., "On the Interpretation of Our Anterior Cruciate Ligament Data", CLINICAL ORTHOPAEDICS, supra at 26. Butler et al. measured the stiffness of the anterior cruciate ligament-bone unit. The stiffness measured for young donors was $182 \pm 56$ kilonewtons per meter and for older donors was $129 \pm 39$ kilonewtons per meter. The maximum force for tissues obtained from young donors was $1730 \pm 66N$.

An object of the present invention is to provide a permanent nonaugmented prosthetic ligament having parameters of strength, flexibility, extension and recovery that at least approximate those of a natural ligament. A further object of the present invention is to provide such a prosthetic ligament that does not depend solely upon bone ingrowth for strengthening the attachment to the bones of the involved joint, and thus, does not require long periods of recuperation before the recipient can resume a full range of normal activity.

SUMMARY OF THE INVENTION

The present invention provides a prosthetic ligament for permanently connecting first and second body members, such as the femur and tibia. The prosthesis of the present invention is a permanent synthetic replacement for a natural ligament and does not depend solely upon the ingrowth of natural tissue to augment the connection between the two body members. Thus, the recipient of the prosthetic ligament can return to a normal range of activity much more quickly than the recipient of a prosthetic ligament requiring augmentation with natural tissue. Furthermore, the mechanical parameters of strength, flexibility, extension and recovery provided by the prosthetic ligament of the present invention at least approximate those of a natural ligament to such an extent that recipients may resume normal activities.

The prosthetic ligament includes a nonaugmented load bearing member having a longitudinal axis for permanently spanning the distance between the first and second body members. The load bearing member is formed from a plurality of biocompatible polyolefin fibers positioned at angles of from about 0° to 55° relative to the longitudinal axis, a range of about 110° in all. Each of the fibers is less than 100 microns in diameter and has a tensile strength greater than or equal to about 50,000 psi.

The load bearing member may define a longitudinal bore therethrough. Means may be disposed within the bore to provide shape for the load bearing member. The shape providing means is preferably made of a biocompatible radiopaque material to permit radiographic visualization of the prosthetic ligament. The shape providing means preferably has a diameter less than or equal to the diameter of the bore and is made from a high strength block copolymer containing silicone oil.

The prosthetic ligament may further include a tear resistant sheath encasing the load bearing member for preventing abrasion of the fibers. The sheath may be a tube friction fit to the load bearing member or may be molded onto the load bearing member. The sheath is preferably made of a high strength block copolymer containing silicone oil.

The load bearing member may be a hollow polypropylene braid which is formed from sixteen four-ply yarns. Each ply of the four-ply yarns may have sixty-eight fibers. The polypropylene braid preferably has a weave angle of between 40° and 48° relative to the longitudinal axis. Polyethylene may also be used to form the load bearing member.

Means, such as eyelets, or looped extensions of the load bearing member, for anchoring the prosthetic ligament to the first and second body members may also be provided.

BRIEF DESCRIPTION OF THE DRAWINGS

The present invention can better be understood by reference to the drawings in which.

DETAILED DESCRIPTION OF THE PREFERRED EMBODIMENT

Figure 1:
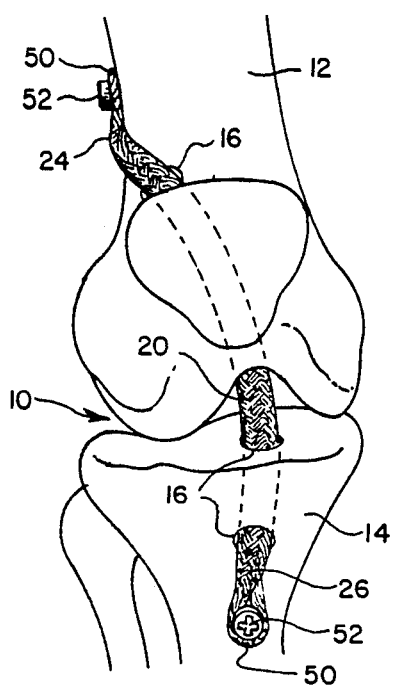
FIG. 1 is a view of the preferred embodiment of the prosthetic ligament of the present invention joining the femur and tibia of a recipient.
Figure 2:
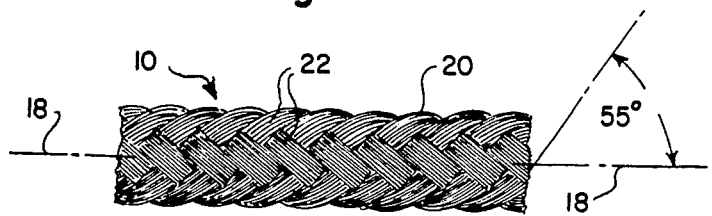
FIG. 2 is a view of a braided load bearing member of the present invention.
Figure 3:
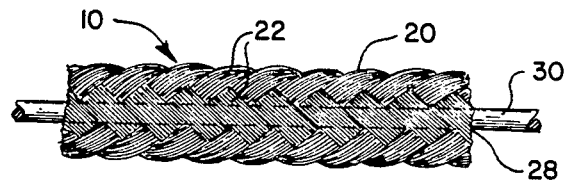
FIG. 3 is a view of the load bearing member of FIG. 2 with an inner core.

FIGS. 1 through 5 illustrate the preferred embodiments of the prosthetic ligament 10 of the present invention. Although the prosthetic ligament 10 is shown as flexibly connecting the femur and tibia, it should be recognized that the prosthetic ligament 10 can be used to connect other skeletal members and, depending upon the means of attachment employed, to support soft tissue organs in place. For purposes of describing the preferred embodiment of the invention, however, the prosthetic ligament 10 is employed to permanently replace the natural cruciate ligament of the human knee.

The prosthetic ligament 10 includes primarily a major load bearing member 20. A core 30 and sheath 40 may also be included. The load bearing member 20 is formed from a plurality of biocompatible polyolefin fibers 22 positioned at angles of from about 0° to 55° relative to the longitudinal axis 18 of the load bearing member 20, a range of about 110° in all. The weave angle provides the load deformation characteristics of the prosthetic ligament 10. A weave angle greater than about 55° relative to the longitudinal axis 18 has been found to elongate or stretch too much when the ligament 10 is under stress. Straight fibers will elongate much less. Angled fibers will elongate more and lower the stiffness in the ligament 10. It has been determined that, depending upon the desired stiffness (a natural cruciate ligament has a stiffness of about 180N/mm), the anatomical location of the prosthetic ligament 10, and the diameter and length of the prosthesis, the weave angle can vary between about 0° and ±55°, inclusive, relative to the longitudinal axis 18. For example, in one embodiment, when the ligament 10 is made of polypropylene and replaces a cruciate ligament of the knee, the weave angle is between 40° and 48°, inclusive. The preferred weave angle varies for different materials. A preferred embodiment is that of a braided member shown in FIG. 2. The braided construction allows utilization of the high-strength fibers as individual units while providing negligible bending resistance. Braiding also allows for the selection of a braiding angle which will result in the optimum load deformation characteristics.

The fibers must be made of a biocompatible organic polymer, preferably polyolefins such as high strength polypropylene or ultrahigh molecular weight polyethylene. Kavesh et al. U.S. Pat. No. 4,413,110 describes a process for the production of ultrahigh molecular weight polypropylene and polyethylene fibers which have a high tenacity and a high tensile modulus. The commercial embodiments of the polyethylene fibers described in the Kavesh patent, have a tensile strength of about 375,000 psi per yarn. The density of each fiber is between 0.5-1.5 g/cc, preferably about 0.97. Each fiber is less than 100 microns in diameter. A plurality of such high strength polyolefin fibers, with each fiber having a tensile strength greater than or equal to about 50,000 psi, woven at the desired angle, provides a high strength load bearing member 10. Numerous fibers add to the life of the ligament 10 because there are numerous surfaces to tolerate the stress and to break in the event of excessive stress before the entire ligament 10 can fail.

The fibers may be assembled to form a porous surface on at least a portion of the load bearing member 20. Pore sizes from about 0 to 100 microns enhance fibrous ingrowth. Pore sizes greater than 100 microns enhance bony ingrowth. Fibrous or bony ingrowth will not occur, however, in those places where sheath 40 covers the load bearing member 20.

For polypropylene, the braided load bearing member 20 is optimally formed from sixteen four-ply yarns. Each ply of the four-ply yarn has sixty-eight high strength polypropylene fibers. Thus, the preferred embodiment of the braided load bearing member 20 of ligament 10 has 4,352 individual fibers. The unit can carry a minimum load of 300 lbs.

Figure 4:
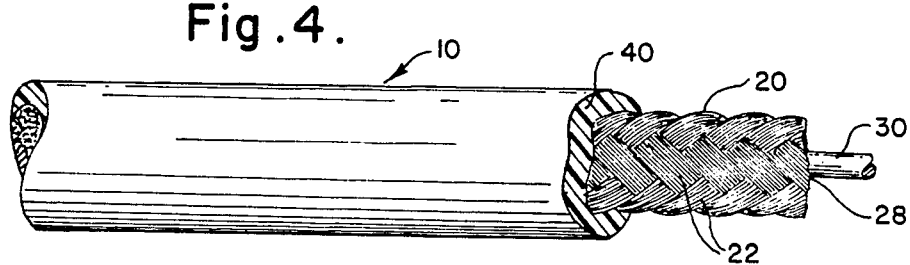
FIG. 4 is a view of the load bearing member of FIG. 2 with an inner core and an outer sheath.
Figure 5:
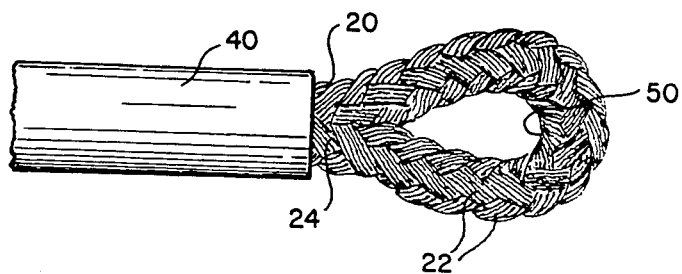
FIG. 5 is a view of one end of the load bearing member of FIG. 2 with a looped extension for anchoring the prosthetic ligament to the recipient.

The prosthetic ligament 10 can be placed in the recipient by any suitable surgical technique. If bone tunnels 16 are used, the load bearing member 20 is preferably encased in a tear resistant sheath 40, as shown in FIG. 4, to protect the fibers 22 of load bearing member 20 from abrasion at the entrance to the tunnels 16.

The sheath 40 may be a tube having an internal diameter equal to or less than the diameter of the load bearing member 20 which is friction fit onto the load bearing member 20. The sheath 40 must be thick enough to withstand the abrasion to which it will be subjected. In the preferred embodiment for use in replacing a cruciate ligament, the sheath 40 is about 1/16 inch thick. The thickness may vary depending upon the desired use of the prosthetic ligament 10.

The sheath 40 may also be extruded onto the load bearing member 20. Care should be taken, however, to avoid over heating the load bearing member 20. Excessive heat can damage the fibers 22. Regardless of how the sheath 40 is applied to the load bearing member 20, the sheath 40 must be relatively thick. It has been determined that merely thinly coating the load bearing member 20 is insufficient because the coating shreds and peels over time. While the drawings show ligament 10 as having a circular cross-section, those skilled in the art will recognize that the cross-section can be elliptical or any other shape suitable for the intended end use of the prosthesis. For example, sheath 40 may have an elliptical cross section to match the shape of a natural ligament. The ligament 10 may also be more narrow at its midportion than at its end portions.

The core 30 is disposed within a longitudinal bore 28 through load bearing member 20 to provide shape for the load bearing member. The core 30 is preferably made of a biocompatible elastomer to which is added a biocompatible radiopaque material which permits radiographic visualization of the prosthetic ligament 10. The material of choice is made of between 5–25%, inclusive, barium sulfate, by weight, in a high strength block copolymer containing silicone oil. Zirconium oxide, titanium oxide or any other suitable radiopaque material may be used in place of barium sulfate. A suitable elastomer is described in Sterling U.S. Pat. No. 4,386,179, and sold commercially under the trademark C-FLEX®. Sheath 40 is preferably also made of C-FLEX®.

Prosthetic ligament 10 includes means, such as the braided eyelets 50 or looped extensions of load bearing member 20, metallic eyelets or surgical staples (not shown), for anchoring the ligament 10 to the skeletal members 12, 14. One braided eyelet 50 is connected to each end 24 and 26 of load bearing member 20. Bone screws 52 connect the braided eyelets 50 to the skeletal members 12, 14. Surgical staples may also be used.

Mechanical tests of the prosthetic ligament 10 with and without sheath 40 were conducted. All of the ligaments tested included the core 30. One series of tests were performed using a high strength polypropylene braid composed of sixteen 4-ply yarns, each ply of the 4-ply yarn having sixty-eight individual fibers. The yarns were braided around a barium sulfate-loaded C-FLEX® core. A C-FLEX® sheath 40 was present in some of the ligaments tested.

The tests included tensile strength and stress relaxation. All tensile strength testing was performed on a Model TMS Instron. An extension meter with 1.59 mm (1/16 in.) discrete gradiations was used to measure elongation of each ligament 10 tested.

The chart below compares test results of the sheathed and unsheathed polypropylene prosthetic ligament 10 having an eliptical cross-sectioned core, the sheathed and unsheathed prosthetic ligament 10 having a circular cross-sectioned core and test results reported by other researchers* for human anterior cruciate ligaments.
*F. Noyes & E. Grood, "The Strength of the Anterior Cruciate Ligament in Humans and Rhesus Monkeys" J. Bone Jt. Surg. 58-A: 1074–1802 (1976)

TABLE I

MECHANICAL PROPERTIES AND TEST PARAMETERS OF HUMAN ANTERIOR CRUCIATE LIGAMENT AND POLYPROPYLENE LIGAMENT PROSTHESIS

|  | Ultimate strength N | Ultimate strain % | Linear stiffness N/mm |
|---|---|---|---|
| Human ACL** | 1730 | 44.3 | 182 |
| Eliptical construction, without sheath | 1620 | 29.0 | 254 |
| Eliptical construction, with C-FLEX ® sheath | 1590 | 70.3 | 123 |
| Circular construction without sheath | 2040 | 32.7 | 322 |
| Circular construction with C-FLEX ® sheath | 2120 | 31.1 | 327 |

|  | Energy to Failure N-m | Strain Rate %/sec |
|---|---|---|
| Human ACL | 10.8 | 100 |

TABLE I-continued

MECHANICAL PROPERTIES AND TEST PARAMETERS OF HUMAN ANTERIOR CRUCIATE LIGAMENT AND POLYPROPYLENE LIGAMENT PROSTHESIS

| Eliptical construction, without sheath | 6.3 | 0.36 |
|---|---|---|
| Eliptical construction, with C-FLEX ®sheath | 13.1 | 0.51 |
| Circular construction without sheath | 10.5 | 0.33 |
| Circular construction with C-FLEX ® sheath | 9.4 | 0.28 |

**Calculations are based on maximum obtained force.

The braided load bearing member 20 was found to have a breaking load of 464 lb; an apparent ultimate tensile strength of 72,600 psi, a modulus of elasticity of 305,000 psi and a stiffness of 1836 lb/in. Each fiber of the braid had an average ultimate tensile strength of 103,000 psi and a modulus of elasticity of 376,000 psi.

A second series of mechanical tests were conducted (see Table II) using a braided load bearing member 20 made of ultrahigh molecular weight polyethylene. Both sheathed and unsheathed ligaments 10 were tested.

TABLE II

|  | With C-FLEX ® Sheath | Without Sheath |
|---|---|---|
| Ultimate Load | 8110 N | 10,100 N |
| Ultimate Elongation | 12.8 mm | 14.2 mm |
| Ultimate Stress* | 383 MPa | 476 MPa |
| Ultimate Strain | 6.7% | 7.5% |
| Energy to Failure | 89 N-m | 121 N-m |
| Stiffness (Linear) | 634 N/mm | 711 N/mm |

*Nominal using cross-sectional area at mid-section of 21.2 mm$^2$ 191 mm (7½") with 19 mm (0.75") eyelets Strain Rate = 0.9%/second

MANUFACTURE OF FIBERS

The polypropylene yarn from which load bearing member 20 is made is obtained by melt spinning the polypropylene fibers in a screw-type extruder. The yarn used to make the braided ligaments employed in the tests discussed above was extruded from a pilot-plant extruder fitted with a spinning head and metering pump, a forced-air quench zone, a spin-finish applicator, twin take-up godets and a winder. A spinneret having 68 orifices and a pack assembly filled with 20–30 mesh ottawa sand supported by two 40 and two 400-mesh stainless steel screens are fitted into the lower portion of the head. The feed zone of the extruder is preset to a temperature of 306±5° C. The metering zone-upper head is preset to a temperature of 277±5° C. and the metering zone-lower head is preset to a temperature of 275±5° C.

Polypropylene pellets (MARLEX TM, Type HGN-020-01, Phillips Petroleum Co.) are fed into the feed hopper of the extruder which is preferably set at a feed rate of about 1.5 to 2.0 lb/h. The feed pressure is preferably set at about 1800 to 2800 psig.

The polypropylene fibers are then oriented on a draw winder to increase the strength of the fibers. The fibers are passed from the feed spools through tensioning guides to a feed godet, and then oriented as they are drawn over a heated plate (120±10° C.) by the draw godet, which rotates at a faster speed than the feed godet. The delivery godet speed is set at about 5–10 ft/min and the draw level is adjusted to about 6:1–8:1.

The oriented fibers are plied on a draw winder where they are passed from four feed spools through tensioning devices and guides to a godet at room temperature and finally to a spool on a constant-tension winder to produce the four-ply yarn.

The four-ply yarn is then placed on each end carrier of a 16 end-carrier braider. The yarn is braided around the radiopaque core 30. When desired, the elastomeric sheath 40 is applied to complete the embodiment of ligament 10 having the sheath.

Polyethylene and polypropylene fibers may be manufactured in accordance with the teachings of Kavesh, et al. U.S. Pat. No. 4,413,110.

What is claimed is:

1. A prosthetic ligament for permanently, flexibly connecting first and second body members comprising:
    a nonaugmented load bearing member having a longitudinal axis for permanently spanning the distance between said first and second body members for providing a prosthetic ligament having parameters of strength, flexibility, extension and recovery that at least approximate those of a natural ligament, said load bearing member being formed into a braid from a plurality of biocompatible high strength polypropylene yarns positioned at angles of from about 0° to 55° relative to said longitudinal axis, each said yarn being comprised of a plurality of fibers, each said fiber being less than 100 microns in diameter and having a tensile strength greater than or equal to about 50,000 psi.

2. The prosthetic ligament recited in claim 1 wherein said load bearing member defines a longitudinal bore therethrough and said prosthetic ligament further comprises means disposed within said bore to provide shape for said load bearing member.

3. The prosthetic ligament recited in claim 2 wherein said shape providing means is made of a biocompatible radiopaque material to permit radiographic visualization of said prosthetic ligament.

4. The prosthetic ligament recited in claim 2 wherein said shape providing means is a solid core having a diameter less than or equal to the diameter of said bore and is made from a high strength block copolymer containing silicone oil.

5. The prosthetic ligament recited in claim 1 or 2 further comprising a tear resistant sheath encasing said load bearing member for preventing abrasion of said fibers.

6. The prosthetic ligament recited in claim 5 wherein said sheath is a tube friction fit to said load bearing member.

7. The prosthetic ligament recited in claim 5 wherein said sheath is extruded onto said load bearing member.

8. The prosthetic ligament recited in claim 5 wherein said sheath is made of a high strength block copolymer containing silicone oil.

9. The prosthetic ligament recited in claim 1 wherein said braid is formed from sixteen four-ply yarns positioned at angles of from about 40° to 48° relative to said longitudinal axis, and each ply of said four-ply yarns has sixty-eight said fibers.

10. The prosthetic ligament recited in claim 1 having a circular cross-section.

11. The prosthetic ligament recited in claim 1 having an eliptical cross-section.

12. The prosthetic ligament recited in claim 1 having a cross-section that varies in size such that the size of the midportion of said ligament is less than or equal to the size of the ends of said ligament.

13. The prosthetic ligament recited in claim 1 wherein at least a portion of said load bearing member forms a porous surface for enhancing fibrous ingrowth.

14. The prosthetic ligament recited in claim 1 wherein at least a portion of said load bearing member forms a porous surface for enhancing bony ingrowth.

15. The prosthetic ligament recited in claim 1 further comprising means for anchoring said prosthetic ligament to said first and second body members.

16. The prosthetic ligament recited in claim 15 wherein said anchoring means are eyelets joined to each end of said load bearing member.

17. The prosthetic ligament recited in claim 16 wherein said eyelets are looped extensions of said load bearing member.

* * * * *

UNITED STATES PATENT AND TRADEMARK OFFICE
CERTIFICATE OF CORRECTION

PATENT NO. : 4,731,084
DATED : March 15, 1988
INVENTOR(S) : Richard L. Dunn et al.

It is certified that error appears in the above-identified patent and that said Letters Patent is hereby corrected as shown below:

Col. 1, line 26, delete "Auogmentation" and substitute therefor --Augmentation--.

Col. 1, line 39, delete "growth" and substitute therefor --ingrowth--.

Col. 5, line 62, after "construction", insert --,--.

Col. 5, line 64, after "construction", insert --,--.

Col. 6, line 9, after "construction", insert --,--.

Col. 6, line 11, after "construction", insert --,--.

Col. 6, line 33, after "Nominal", insert --,--.

Col. 6, line 34, after "21.2mm$^2$", insert --,--.

Col. 6, line 34, delete "Strain Rate = 0.9%/second".

UNITED STATES PATENT AND TRADEMARK OFFICE
CERTIFICATE OF CORRECTION

PATENT NO. : 4,731,084
DATED : March 15, 1988
INVENTOR(S) : Richard L. Dunn et al It is certified that error appears in the above-identified patent and that said Letters Patent is hereby corrected as shown below:

Col. 6, line 35, insert --Strain Rate= 0.9%/second --.

Signed and Sealed this

Eighth Day of November, 1988

Attest:

DONALD J. QUIGG

Attesting Officer

Commissioner of Patents and Trademarks